United States Patent [19]

Del Rossi et al.

[11] Patent Number: 5,185,484
[45] Date of Patent: Feb. 9, 1993

[54] DEHYDROCYCLIZATION AND REFORMING CATALYST

[75] Inventors: Kenneth J. Del Rossi, Mantua; Garry W. Kirker, Washington Township, Bergen County, both of N.J.; Albin Huss, Jr., Chadds Ford, Pa.

[73] Assignee: Mobil Oil Corp, Fairfax, Va.

[21] Appl. No.: 457,211

[22] Filed: Dec. 26, 1989

[51] Int. Cl.$^5$ ................................................ C07C 2/52
[52] U.S. Cl. .................................................... 585/419
[58] Field of Search ......................................... 585/419

[56] References Cited

U.S. PATENT DOCUMENTS

| | | | |
|---|---|---|---|
| 3,755,486 | 8/1973 | Oishi et al. | 585/419 |
| 3,775,502 | 11/1973 | Oishi | 585/419 |
| 4,435,283 | 3/1984 | Buss et al. | 208/138 |
| 4,627,912 | 12/1986 | Field | 208/138 |
| 4,652,360 | 3/1987 | Dessau | 585/419 |
| 4,711,770 | 12/1987 | Skeels et al. | 502/79 |
| 4,832,824 | 5/1989 | Vaughan et al. | 208/138 |
| 4,836,911 | 6/1989 | Skeels et al. | 585/467 |
| 4,840,930 | 6/1989 | LaPierre et al. | 502/77 |
| 4,867,864 | 9/1989 | Dessau | 585/421 |

*Primary Examiner*—H. M. S. Sneed
*Assistant Examiner*—James Saba
*Attorney, Agent, or Firm*—Alexander J. McKillop; Charles J. Speciale; Marina V. Schneller

[57] ABSTRACT

A Pt/Ba/USY catalyst prepared with a high $SiO_2/Al_2O_3$ ratio USY gives improved aromatics selectivity compared to other Pt/USY containing catalysts. The improved selectivity is a result of the method of catalyst preparation which includes incorporation of a Group IIA metal after platinum incorporation.

22 Claims, 2 Drawing Sheets

DEHYDROCYCLIZATION AND REFORMING CATALYST

FIELD OF THE INVENTION

Catalysis of dehydrocyclization and reforming processes is effected in the presence of a low acidity or non-acidic composition containing at least one Group VIII noble metal and a chemically dealuminated ultrastable Y zeolite treated in the final stage of synthesis with a soluble source of Group IIA metal cation. These processes exhibit low selectivity for light gas production.

BACKGROUND OF THE INVENTION

Dehydrocyclization of aliphatic $C_6+$ compounds produces known aromatic compounds. For example, benzene and toluene are the products of n-hexane and n-heptane dehydrocyclization reactions.

Dehydrocyclization occurs in catalytic reforming which is a process in which hydrocarbon molecules are rearranged, or reformed in the presence of a catalyst. The molecular rearrangement results in an increase in the octane rating of the feedstock. Thus, during reforming low octane hydrocarbons in the gasoline boiling range are converted into high octane components by dehydrogenation of naphthenes and isomerization, dehydrocyclization and hydrocracking of paraffins.

By way of illustration, the significance of those reactions in reforming can be gleaned from a review of the following table from "Catalysis," Vol VI, P.H. Emmett (ed). Copyright 1958 by Litton Educational Publishing Company:

| Octane Numbers of Pure Hydrocarbons | |
|---|---|
| Hydrocarbon | Blending research octane number (clear) |
| Paraffins: | |
| n-Butane | 113 |
| n-Pentane | 62 |
| n-Hexane | 19 |
| n-Heptane | 0 |
| n-Octane | −19 |
| 2-Methylhexane | 41 |
| 2,2-Dimethylpentane | 89 |
| 2,2,3-Trimethylbutane | 113 |
| Naphthenes (cycloparaffins): | |
| Methylcyclopentane | 107 |
| 1,1-Dimethylcyclopentane | 96 |
| Cyclohexane | 110 |
| Methylcyclohexane | 104 |
| Ethylcyclohexane | 43 |
| Aromatics: | |
| Benzene | 99 |
| Toluene | 124 |
| 1,3-Dimethylbenzene | 145 |
| Isopropylbenzene | 132 |
| 1,3,5-Trimethylbenzene | 171 |

Naphtha reforming may also be utilized for the production of benzene, toluene, ethylbenzene, and xylene aromatics. A valuable by-product of naphtha reforming is hydrogen, which may be utilized for hydrotreating and upgrading of other hydrocarbon fractions. Generally, the molecular rearrangement of molecular components of a feed, which occurs during reforming, results in only slight, if any, changes in the boiling point of the reformate (the product of reforming), compared to that of the feed. Accordingly, reforming differs from both cracking and alkylation, both refinery processes, each of which does result in changes of boiling range of the product compared to the feed. That is, in cracking, large molecules are cracked into smaller ones; whereas, in alkylation small molecules are rebuilt into larger molecules.

The most important applications of the reforming process are as an octane upgrader and as a route to premium gasoline. Catalytic reforming is the only refining process that is capable of economically making a gasoline component having high clear research octane ratings. The charge to the reformer (straight-run, thermal, or hydrocracker naphtha) is usually available in large quantities and is of such low quality that most of it would be unsaleable without reforming.

A correlative use of catalytic reforming is in its ability to produce gasolines of acceptable volatility over a wide range of yields, through proper selection of feedstock and/or operating conditions. The refiner is thus able to vary the yield of gasoline very substantially to meet demand fluctuations. For European demand patterns, where gasoline sales are limiting and it is desired to produce as much middle distillate as practicable, the reformer can be operated on a lighter, lower volume of naphtha to minimize gasoline production while maintaining high crude runs.

Hydrogen, although often considered a by-product, is still a valuable output from the reformer. Normally, it is produced in amounts ranging from 300 to 1200 SCF/Bbl, depending on the type of feed stock and reformer operating conditions. Reformer hydrogen is used to remove unwanted contaminants from reformer feed stocks, for hydrodesulfurization of distillates, hydrocracking of heavy fractions, hydrotreating of lubes and various chemical operations. Hydrogen availability and utilization is expected to assume increasing importance as pollution restrictions lead to increasing hydroprocessing in future years.

The importance of reforming is reflected by data which indicates that finished pool gasoline is about 35% reformate in complex refineries, but can run as high as 80% in topping-reforming refineries. As lead is phased out of gasoline, more and more straight run stocks which are now blended directly into gasoline will be reformed. All current commercial reformers use a platinum containing catalyst with a hydrogen recycle stream. Within this broad definition, there are a great number of different process designs. More than 75% of the industry's reforming capacity is classified as semi-regenerative. A semi-regenerative reformer is one which runs until the catalyst is coked and then is shut down and regenerated. The time period between regenerations varies from several months to as long as 1½ years.

Within the category of semi-regenerative reforming, a further breakdown can be made on the basis of operating pressure. Units with separator pressures of 450 psig or higher are considered high pressure units. Those with pressures of 300 psig or less are called low pressure units. Anything in between is intermediate pressure. Most of the older units are high pressure, while the newer designs are low or intermediate pressure. Lower pressures give better reformate yields at a given octane level.

Another type of reformer is the cyclic variety. A cyclic unit has the reactors manifolded in such a way that any reactor can be taken out of reforming service and regenerated while the other reactors are still operating. The time period between regenerations for a cyclic reactor varies from 2 to 10 days. All cyclics are low pressure.

A third type of reformer that has recently been commercialized is the continuous unit. In this type of reformer, catalyst is withdrawn from the unit during reforming, regenerated in small batches in separate regeneration facilities and then replaced in the unit. The regeneration period for continuous units is about one month. As in the case for cyclic units, all continuous units are low pressure.

Prior to about 1950 chromium oxide or molybdenum oxide supported on alumina were used to effect the two functions of a reforming catalyst. The hydrogenation-dehydrogenation function for paraffin olefin conversion during reforming is effected by the metals chromium and molybdenum and more recently platinum, rhenium, admixtures thereof and noble-metal containing trimetallic alloys. Isomerization activity was provided by the acidified alumina.

From the commercialization of platinum reforming in the middle 1950's to the late 1960's, there were no significant improvements in reforming catalysts.

In the late 1960's a dramatic breakthrough in reforming catalysts occurred. This was the introduction of the platinum-rhenium bimetallic catalysts. These catalysts have greatly improved stability compared to platinum-only catalysts. By way of background, the platinum and platinum bimetallic catalysts were generally supported on carriers.

The standard dual functional reforming catalysts exhibited high selectivity for cracking. Recently, the patent literature has started to recognize the use of platinum and non-acidic zeolite containing catalyst compositions in reforming. It has been reported that nonacidic catalysts are superior to the dual functional catalyst in selectivities, for example, those nonacidic catalysts based on zeolite X, Y, L, omega and mordenite. J. R. Bernard, PROCEEDINGS OF THE FIFTH INTERNATIONAL ZEOLITE CONFERENCE, Zeolite Conference, p686–695 (Naples 1980).

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), zeolite ZSM-35 (U.S. Pat. No. 4,016,245), and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

SUMMARY OF THE INVENTION

The invention relates to a catalyst for dehydrocyclization of paraffins containing at least six carbon atoms. The dehydrocyclization catalyst is comprised of a noble metal containing composite, wherein the composite contains a de-aluminated zeolite USY (ultrastable Y). The composite is barium exchanged in the final stage of synthesis to reduce cracking activity. Accordingly, one advantage which can inhere in the invention is a decrease in light gas production and an increase in $C_5+$ liquid yields.

DETAILED DESCRIPTION OF THE INVENTION

Figure 1:
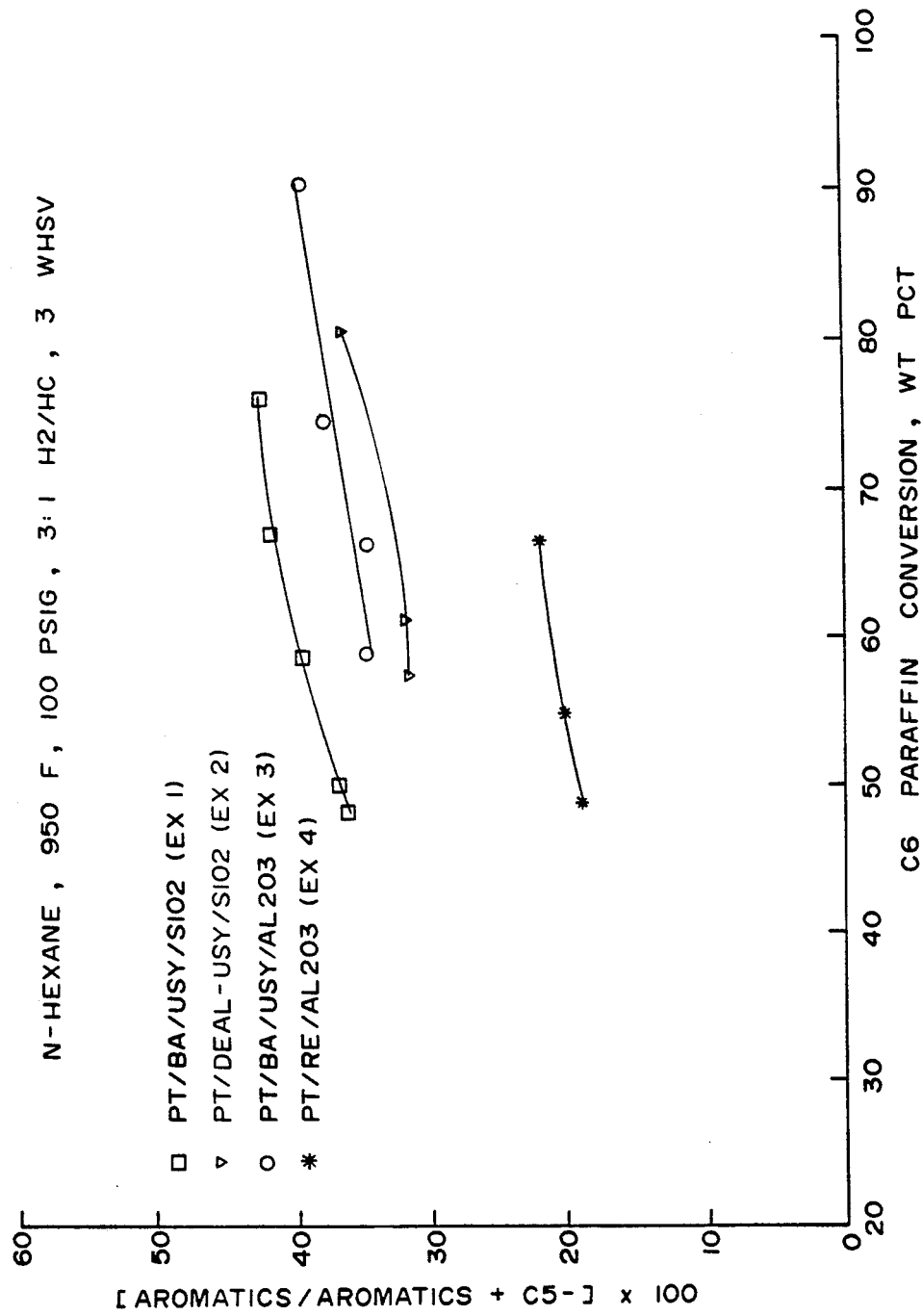
FIG. 1 is a graph of aromatic product selectivity plotted against $C_6$ paraffin conversion.

Dehydrocyclization, in accordance with the invention is undertaken by passing the $C_6+$ paraffin containing feed over the catalyst described below, at a temperature ranging from about 800° to 1100° F.; a pressure of from about 0 psig to about 400 psig; a hydrogen/feed ratio of 0.1 to 10, preferably 2 to 4; and a liquid hourly space velocity (LHSV) of 0.5 to 50, preferably of about 2 to 10.

DEHYDROCYCLIZATION FEEDSTOCKS

The feedstock charge can be at least one $C_6+$ paraffin; or it can be straight run, thermal or hydrocracker naphthas or any other naphtha.

Exemplary $C_6+$ compounds and naphtha components include n-hexane, 2-methylpentane, 3-methylpentane, n-heptane, 2-methylhexane, 3-methylhexane, 3-ethyl-pentane, 2,5-dimethylhexane, n-octane, 2-methylhexane, 3-methylhepatane, 4,methylheptane,3-ethylhexane, n-nonane, 2-methyloctane, 3-methyl-octane, n-decane, and the like.

Preferably the naphtha is a paraffin rich naphtha, particularly rich in $C_6$ to $C_{12}$ paraffins. The $C_6$ and $C_7$ paraffins are generally difficult to reform selectively using conventional catalysts (such as chlorided Pt-alumina).

Naphthas exhibit boiling point temperature ranges of up to about 400° F. The light naphtha fraction thereof will exhibit a boiling point temperature range of from about 80° to about 250° F.

Initial hydrotreating of the feedstock serves to convert sulfur, nitrogen and oxygen derivatives of hydrocarbon to hydrogen sulfide, ammonia, and water while depositing metal contaminant from hydrodecomposition of any organo-metal compounds. Hydrotreating of feedstocks is described by B. C. Gates et al, "Chemistry of Catalytic Processes", p. 390-396, McGraw-Hill, New York, 1979, which is incorporated by reference herein.

DEHYDROCYCLIZATION CATALYST

The catalyst of the invention comprises a strong dehydrogenation/hydrogenation metal and a dealuminated ultrastable zeolite Y in a Group IA and/or Group IIA metal-exchanged form. The ultrastable Y has a framework silica:alumina mole ratio of at least 50. The ultrastable Y of a framework silica:alumina mole ratio greater than 50 used in the invention is preferably chemically dealuminated. Chemical dealumination results in less debris or residue in the zeolite pores compared to dealumination by conventional hydrothermal techniques.

Alternatively, a combination of hydrothermal, thermal and chemical treatments may be used to prepare the USY by procedures known to those skilled in the art.

The catalyst comprises the dehydrogenation metal in an amount ranging from 0.01 to 10 weight percent and preferably from 0.2 to 0.8 weight percent. This component can be a Group VIII metal; it can be those including platinum; palladium, platinum-rhenium; platinum with iridium; rhenium, rhodium or mixtures thereof; but preferably, it is platinum.

Generally, zeolites are used in acidic form, for example, by treating the as synthesized zeolite with a source of $NH_4+$ to exchange at aluminum sites and followed by calcining to evolve $NH_3$, thereby leaving a proton at the aluminum site. The term "acidic" as used herein refers to the catalytic effect of zeolites, to act as strong Bronsted acids which can crack large molecules to lower molecular weight molecules.

However, in accordance with the invention, the zeolite ultrastable Y is in a form in which the framework aluminum sites contain at least in part, rather than protons which render the zeolite acidic, a cation selected from Group IA or Group IIA. Preferably, the cation is $Ba^{2+}$. The term "low-acidic" as used herein, to define the catalyst composition relates to reduction of the acid content of the zeolite, by ion exchange of at least 25% of the available cation exchange sites using Group IA and/or IIA cations, preferably at least 50% of the sites are ion exchanged and most preferably at least 75% of the sites are exchanged. The cation used for the exchange is preferably barium (2+) and preferably the exchange is performed subsequent to inclusion of the Group VIII metal and subsequent to the thermal treatment of the Group VIII metal containing zeolite substrate.

Preferably, the soluble source of barium cations is $Ba(OH)_2$ or $Ba(NO_3)_2$ to avoid inclusion of contaminating cations in the zeolite. Exchange is undertaken at a pH of greater than 7. The molar ratio of barium to zeolite aluminum can range from about 0.1 to 10.

If the catalytic composition contains a binder, which is in itself acidic, then the zeolite and the binder are rendered non-acidic simultaneously. In specific embodiments below, the treatment to render them neutral is subsequent to the Group VIII metal incorporation.

Preferably, the Group VIII metal is incorporated into the zeolite after calcination of the zeolite, in the form of an aqueous solution. The aqueous solution contains at least one Group VIII metal salt to exchange or sorb ionic Group VIII metal into the zeolite. Illustrative of suitable platinum compounds are chloroplatinic acid, platinum chloride, platinum amine complexes, and the like.

After contact of a slurry of the zeolite with the aqueous solution of the Group VIII metal compounds, the zeolite material is washed and dried at a temperature of about 100° C.

Thereafter, the Group VIII metal-containing zeolite is subjected to a thermal treatment, by heating the zeolite substrate in contact with a reducing, oxidizing, or inert environment. The environment can be air, hydrogen, nitrogen, or the like. This thermal treatment is conducted at a temperature ranging between about 150° to 550° C., for a period of time sufficient to achieve the desired conversion state, contact time ranging from between about 0.2 to 10 hours.

As noted above the zeolite is preferably composited with a silica binder which can comprise 1 to 90 weight percent of the composition. However, conventional binders such as alumina, zirconia, and silica-alumina, may be used. Naturally occurring clays which can be composited with the new crystal include the montmorillonite and kaolin familes which include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the present composition can be composited with a porous matrix material such as aluminum phosphate, silica-alumina, silica-magesia, silica-zirconia, silica-thoria, silica-beryllia, silica-titania as well as ternary compositions such as silica-alumina-thoria, silica-alumina-zirconia silica-alumina-magnesia and silica-magnesia-zirconia. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite.

The following examples serve to illustrate the invention, rather than to limit it.

Examples

EXAMPLE 1

A high silica, Pt/Ba/USY/SiO$_2$ catalyst was prepared as detailed hereinafter. A commercial USY (65 wt%) characterized by a chemical SiO$_2$/Al$_2$O$_3$ molar ratio of about 14, framework SiO$_2$/Al$_2$O$_3$ of greater than about 100, B.E.T. surface area greater than 500 m$^2$/gm, a U.C.S. of 24.3A (which is less than 24.35A) and a high degree of crystallinity was admixed with 26.2% amorphous precipitated silica (Hi Sil 233) and 8.8% colloidal silica (LUDOX HS-30), mulled and extruded to form an extrudate of 1/16 inch diameter; the extrudate was dried at 250° F. The extrudate was then ammonium nitrate (5 ml of 1N NH$_4$NO$_3$/1g of catalyst) exchanged two times at 80° F.; the exchanged extrudate was washed with deionized water and dried at 250° F. and then heated at a rate of 5° F./min. to 1000° F. and air calcined for 3 hours at 1000° F.

The calcined extrudate was then steamed at 1025° F. for 24 hours in 100% steam.

The steamed and calcined extrudate was then humidified; exchanged with 0.045 N (Pt(NH$_3$)$_4$Cl$_2$) for 8 hours; washed with deionized water; dried at 150° F. and calcined in air.

The calcined platinum containing ultrastable Y was then subjected to humidity and Ba(NO$_3$)$_2$ exchanged with 0.28 N Ba solution for four hours at a pH of 8. The catalyst was dried at 150° F., and calcined in air.

The resulting catalyst contained 0.42 weight percent platinum and 1.20 weight percent barium.

EXAMPLE 2

A platinum dealuminated USY catalyst, Pt/Deal-USY/SiO$_2$, was prepared for comparison with the catalyst of the present invention, Pt/Ba/USY/SiO$_2$, to demonstrate the advantage of alkaline exchange. A mixture containing 65 wt % commercial USY characterized by a chemical SiO$_2$/Al$_2$O$_3$ molar ratio of ~ 5 and a B.E.T. surface area of greater than 450 ml 2/6, 8.8 wt % collodial silica (Ludox) and 26.2 wt % amorphous precipitated silica (HiSil 233) was mulled and extruded to 1/16" diameter. The extrudate was dried at 250° F., then calcined at 1000° F. for three hours in air. The extrudate was exchanged three times at room temperature with 1N NH$_4$NO$_3$ solution, dried at 250° F., and calcined at 1000° F. for three hours in air.

The extrudate was steamed at 1200° F. for ten hours in one atmosphere steam, then treated two times at room temperature for one hour with 1N HNO$_3$ solution. The extrudate was dried at 250° F., and calcined at 1000° F. for three hours in air. The extrudate was subjected to a second steaming at 1200° F. for ten hours in one atmosphere steam. The steamed extrudate was treated two times at room temperature for one hour with 1N HNO$_3$ solution, dried at 250° F., and calcined at 1000° F. for one hour in air.

The extrudate was exchanged for four hours with a Pt(NH$_3$)$_4$Cl$_2$/NH$_4$OH solution at a pH of 9, washed with deionized water, dried at 250° F., and calcined at 660° F. for three hours in air. The final catalyst contained 0.6 wt % platinum.

EXAMPLE 3

A Pt/Ba/USY/Al$_2$O$_3$ catalyst was prepared for comparison with the catalyst of the current invention, Pt/Ba/USY/SiO$_2$, to demonstrate the advantage of barium exchange in the final stage of synthesis. A mixture containing 65 wt % USY, (the same USY as in Example 1) and 35 wt % Al$_2$O$_3$ (Kaiser SA) was mulled and extruded to 1/16" diameter. The extrudate was dried at 250° F. and calcined at 1000° F. for three hours in air.

The extrudate was exchanged two times with 0.56 M barium nitrate solution, and dried at 250° F. The exchange extrudate was then calcined at 1000° F. for three hours in air.

The extrudate was exchanged with Pt(NH$_3$)$_4$Cl$_2$ solution at pH of nine for four hours, then washed with deionized water and calcined at 660° F. for three hours in air. The final catalyst contained 0.6 wt % platinum.

EXAMPLE 4

A commercial Pt/Re/Al$_2$O$_3$ reforming catalyst was obtained for comparison with the catalyst of the present invention to demonstrate the selectivity advantage of USY-based catalysts for dehydrocyclization of paraffins. The Pt/Re/Al$_2$O$_3$ catalyst contained 0.22 wt % Pt, and 0.44 wt % Re on gamma-Al$_2$O$_3$. The catalyst was supplied in the sulfided state by UOP, the manufacturer.

EXAMPLE 5

The Pt catalysts were evaluated in a fixed bed pilot unit equipped with a ½ inch ID stainless steel reactor. In a typical run, 4 grams (approximately 10 cc) of 14/24 mesh catalyst were loaded into the reactor. The catalyst bed was heated at a rate of 220° F./hour in 100 cc/min of flowing hydrogen to 950° F. and then held at this temperature for one hour. Dehydrocyclization data were then obtained at 950° F., 100 psig, 3:1 H$_2$/HC and 3 WHSV with a 100% n-hexane feed.

Figure 2:
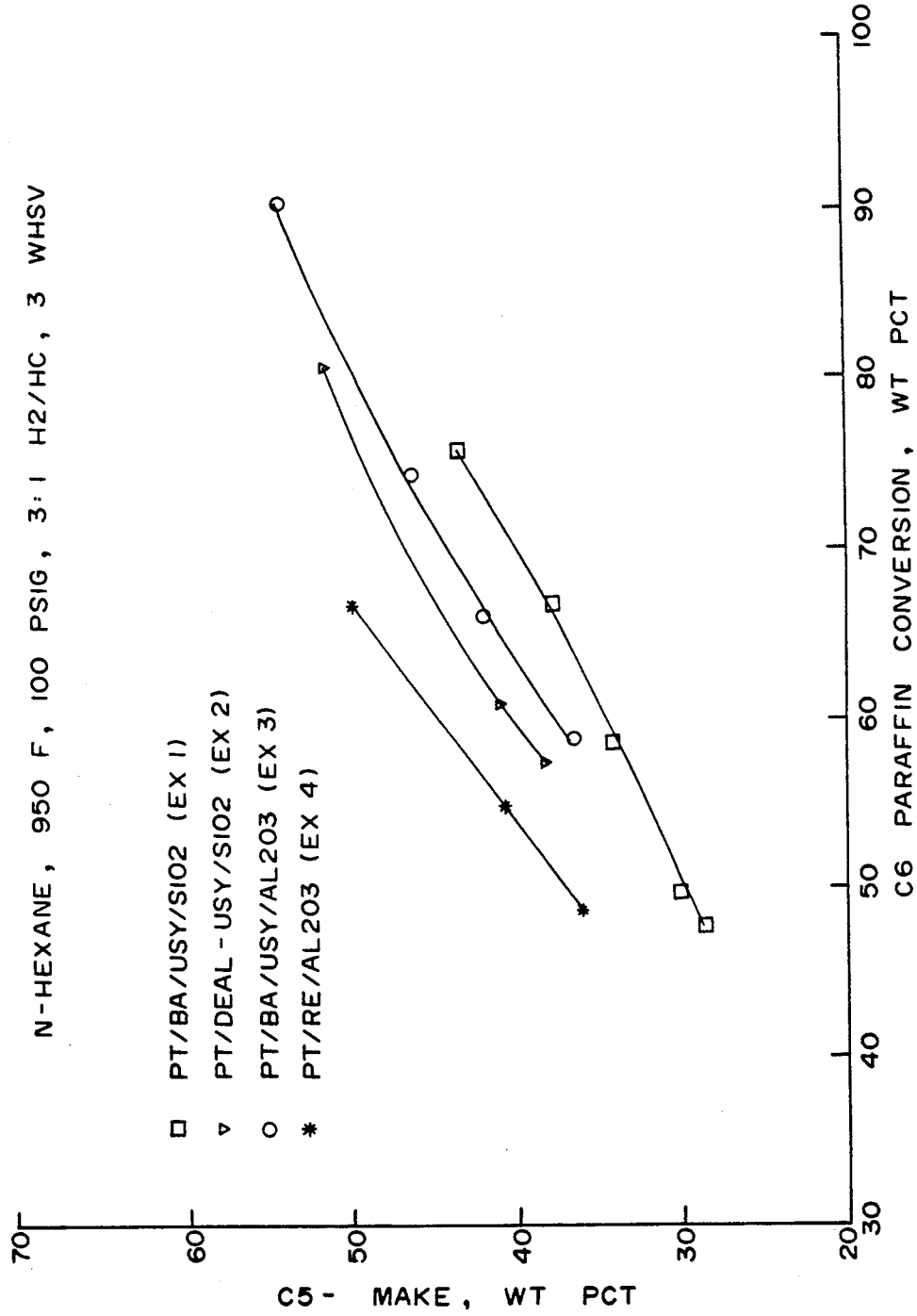
FIG. 2 is a graph of $C_5-$ make plotted against $C_6$ paraffin conversion.

The data for the Pt/Ba/USY/SiO$_2$ catalyst of the current invention are given in Table 1 along with data on other USY-based catalyst and a conventional Pt/Re/Al$_2$O$_3$ reforming catalyst. Aromatics selectivity, as listed in Table 1, is defined as the weight percent aromatics in the product divided by the sum of aromatics and C5— produced. Aromatics selectivity and C$_6$ paraffin conversion for each catalyst are graphically compared in FIG. 1. The high silica Pt/Ba/USY/SiO$_2$ catalyst is clearly the most selective for aromatics at comparable C$_6$ paraffin conversion. Furthermore, this catalyst yields less hydrocracked product at comparable C$_6$ paraffin conversions, as illustrated in FIG. 2.

The high silica Pt/Ba/USY/SiO$_2$ catalyst claimed herein is more selective for the conversion of low octane paraffins to high octane aromatics, and shows lower activity for hydrocracking of paraffins when compared to previously examined USY-based and conventional Pt/Re/Al$_2$O$_3$ reforming catalysts. Consequently, this catalyst may be used to convert low octane paraffinic streams to high octane gasoline with lower yield loss than alternative USY-based and conventional reforming catalysts.

TABLE 1

| REACTIVITY DATA WITH N-HEXANE FEED | | | | | | | | | | | | | | | |
|---|---|---|---|---|---|---|---|---|---|---|---|---|---|---|---|
| | Example 1 Pt/Ba/USY/SiO$_2$ | | | | | Example 2 PT/DEAL-USY/SiO$_2$ | | | Example 3 PT/Ba/USY/Al$_2$O$_3$ | | | | Example 4 Pt/Re/Al$_2$O$_3$ | | |
| HOS | 1.0 | 6.0 | 26.0 | 41.0 | 56.0 | 7.0 | 47.0 | 56.0 | 1.0 | 10.0 | 25.0 | 45.0 | 3.0 | 28.0 | 44.0 |
| C$_5$−, Wt PCT | 43.1 | 37.6 | 34.2 | 29.9 | 28.4 | 51.0 | 40.7 | 38.1 | 54.0 | 45.7 | 41.7 | 36.5 | 49.6 | 40.6 | 36.0 |
| C$_6$+ (P + N) | 26.2 | 36.1 | 42.6 | 53.2 | 55.7 | 20.4 | 40.8 | 44.6 | 11.4 | 27.3 | 36.7 | 44.5 | 34.2 | 44.7 | 51.5 |
| Benzene | 27.3 | 23.2 | 19.1 | 15.6 | 14.3 | 25.1 | 16.9 | 15.3 | 28.9 | 25.1 | 20.5 | 17.8 | 9.2 | 5.8 | 4.3 |
| C$_7$+ Aromatics | 3.4 | 3.1 | 2.6 | 1.4 | 1.6 | 3.4 | 1.6 | 2.0 | 5.5 | 1.9 | 1.1 | 1.2 | 4.3 | 4.2 | 3.9 |
| Aromatics Selectivity | 41.7 | 41.2 | 38.8 | 36.3 | 35.9 | 35.9 | 31.3 | 31.2 | 38.9 | 37.1 | 34.1 | 34.2 | 21.4 | 19.8 | 18.6 |

What is claimed is:

1. A process for converting a paraffin containing at least six carbon atoms to an aromatic compound, which process exhibits a high aromatic product selectivity, comprising contacting said paraffin with a catalyst, under dehydrocyclization conditions, wherein the catalyst comprises ultrastable Y having a framework silica:alumina mole ration of greater than 50; a catalitically effective amount of platinum and barium;

wherein the ultrastable Y has cation exchange sites and wherein at least 25% if the available cation exchange sites are exchanged with said barium; and producing at least one aromatic compound with said selectivity which is defined by the formula $$\frac{wt\ \%\ aromatics}{wt\ \%\ aromatics\ plus\ wt\ \%\ C_5\ minus\ products} \times 100.$$

2. A process for converting a paraffin containing at least six carbon atoms to an aromatic compound, which process exhibits a high aromatic product selectivity, comprising contacting said paraffin with a catalyst, under dehydrocyclization conditions, wherein the catalyst comprises a composition of ultrastable Y having a framework silica:alumina mole ratio of greater than 50; a catalitically effective amount of platinum; and barium;

wherein the ultrastable Y has cation exchange sites and wherein at least 25% of the available cation exchange sites are exchanged with said barium; wherein the catalyst is formed by treating the ultrastable Y with Group VIII metal and is subsequently treated with a soluble source of barium; and producing at least one aromatic compound with said selectivity which is defined by the formula $$\frac{wt\ \%\ aromatics}{wt\ \%\ aromatics\ plus\ wt\ \%\ C_5\ minus\ products} \times 100.$$

3. The process of claim 1, wherein the catalyst further includes a non-acidic carrier.

4. The process of claim 1, wherein the catalyst further includes a silica carrier.

5. The process of claim 1, wherein the catalyst consists essentially of said composition and a silica carrier.

6. The process of claim 1, wherein the catalyst consists essentially of said composition and a non-acidic carrier.

7. The process of claim 1, wherein said conditions include a temperature of from about 800° to 1100° F.; preferably 950° to 1000° F., a pressure of from about 0 psig to 400 psig; preferably 50 to 150 psig, a hydrogen/feed ratio of 0.1 to 10; preferably 2 to 5, and a liquid hourly space velocity (LHSV) of 0.5 to 50; preferably 2 to 10.

8. The process of claim 1, wherein the catalyst contains 0.1 wt % to 5.0 wt % barium.

9. The process of claim 1, wherein the catalyst contains 0.1 wt % to 10 wt % Group VIII metal.

10. The process of claim 9, wherein the Group VIII metal is selected from the group consisting of platinum, iridium, palladium, ruthenium, and rhenium.

11. The process of claim 1, wherein the paraffin is provided in the form of a naphtha feedstock.

12. The process of claim 1, wherein the paraffin is a hydrocarbon selected from the group consisting of $C_nH_{2n+2}$ ($n \geq 6$) and $C_nH_{2n}$ ($n \geq 6$).

13. The process of claim 2, where said catalyst is non-acidic.

14. The process of claim 2 wherein the catalyst further includes a silica carrier.

15. The process of claim 2 wherein the catalyst consists essentially of said composition and a silica carrier.

16. The process of claim 2 wherein the catalyst consists essentially of said composition and a non-acidic carrier.

17. The process of claim 2, wherein said composition is non-acidic.

18. The process of claim 2, wherein said conditions includes a temperature of from about 800° to 1100° F.; a pressure of from about 0 psig to 400 psig; a hydrogen/feed ratio of 0.1 to 10; and a liquid hourly spaced velocity (LHSV) of 0.5 to 50.

19. The process of claim 2, wherein the composition contains 0.1 to 5.0 wt % barium.

20. The process of claim 2, wherein the composition contains 0.1 to 10.0 wt % Group VIII metal.

21. The process of claim 20, wherein the Group VIII metal is selected from the group consisting of platinum, iridium, palladium, ruthenium, and rhenium.

22. The process of claim 2 wherein the paraffin is provided in a naphtha feedstock.

* * * * *